United States Patent [19]

Hiramatsu et al.

[11] Patent Number: 5,512,599

[45] Date of Patent: Apr. 30, 1996

[54] PROCESS FOR THE PRODUCTION OF METHANOL

[75] Inventors: Yasushi Hiramatsu; Osamu Hashimoto; Shoji Uematsu, all of Niigata; Toshio Koseki, Tokyo, all of Japan

[73] Assignee: Mitsubishi Gas Chemical Company, Inc., Tokyo, Japan

[21] Appl. No.: 329,828

[22] Filed: Oct. 27, 1994

[30] Foreign Application Priority Data

Oct. 27, 1993 [JP] Japan .................................... 5-269117

[51] Int. Cl.$^6$ ...................................................... C07C 27/00
[52] U.S. Cl. ............................................................. 518/703
[58] Field of Search ............................................. 518/703

[56] References Cited

U.S. PATENT DOCUMENTS

| | | | |
|---|---|---|---|
| 4,666,680 | 5/1987 | Lewis | 422/191 |
| 4,666,945 | 5/1987 | Osugi et al. | 518/713 |
| 4,782,096 | 11/1988 | Banquy | 518/704 |
| 4,956,392 | 9/1990 | Saito et al. | 518/712 |
| 4,994,093 | 2/1991 | Wetzel et al. | 518/703 |
| 5,112,578 | 5/1992 | Murayama et al. | 422/197 |
| 5,156,821 | 10/1992 | Murayama | 422/191 |

FOREIGN PATENT DOCUMENTS 0329292 8/1989 European Pat. Off. .
2179366 4/1987 United Kingdom .

*Primary Examiner*—Werren B. Lone
*Attorney, Agent, or Firm*—Wenderoth, Lind & Ponack

[57] ABSTRACT

A process for the production of methanol, which exhibits high energy efficiency and permits the production of methanol with apparatus of which the production capacity can be increased, the process comprising a primary reforming step of catalytically reacting a hydrocarbon with steam, a partial oxidation step of partially oxidizing a gas fed from the above primary reforming reaction step by adding an oxygen gas, a secondary reforming step of catalytically reacting a gas fed from the above partial oxidation step with steam, a step of using a high-temperature gas obtained from the secondary reforming reaction step, as a heat source for the primary reforming step, a synthesis gas preparation step of separating steam from the gas used as the above heat source to prepare a synthesis gas, and a methanol synthesis step of introducing the synthesis gas into a methanol synthesis reactor using a fluid catalyst, wherein:

the molar ratio of hydrogen to carbon oxides in the feed gas to into the methanol synthesis reactor, represented by $[H_2/(2CO+3CO_2)]$, is set at from 1.0 to 2.7, the molar ratio of $CO_2/CO$ in the feed gas into the methanol synthesis reactor is set at from 0.6 to 1.2, a gas from the methanol synthesis reactor is partially introduced into the methanol synthesis reactor as a circulating gas together with the synthesis gas.

9 Claims, 4 Drawing Sheets

PROCESS FOR THE PRODUCTION OF METHANOL

FIELD OF THE INVENTION

The present invention relates to a process for the production of methanol, and more specifically to a process for the synthesis of methanol from hydrocarbons with a fluidized bed catalytic reactor.

PRIOR ART OF THE INVENTION

Methanol is used in large amounts since it is almost free from environmental pollution and easy to transport, and it is demanded to develop an ultra-large scale apparatus capable of producing 5,000 tons/day, 10,000 tons/day or more of methanol.

In recent years, in order to cope with such an ultra-large scale apparatus for producing methanol for use as a fuel, the development of a fluidized bed catalyst reactor is under way. For example, JP-A-60-84142, JP-A-60-122040 and JP-A-60-106534 (corresponding to U.S. Pat. No. 4,666,945) disclose methods for the production of fluid catalysts for the synthesis of methanol. Further, JP-A-63-211246 (corresponding to U.S. Pat. No. 4,956,392) discloses catalysts and reaction conditions for the synthesis of methanol with a fluidized bed.

The largest problem in the development of the above large-scale apparatus for the production of methanol is to increase the capacity of a gas-reforming apparatus for the production of a synthetic gas from hydrocarbons. A conventional steam-reforming apparatus uses the system of externally heating reaction tubes in a reforming furnace, and when the capacity of an apparatus for the production of methanol is increased, the limit of the capacity of the apparatus is 1,500 to 2,000 tons/day.

A method using the combination of a steam-reforming and a partial oxidation is attracting attention as a method of gas reforming with a large-scale apparatus. This method is carried out as follows. A hydrocarbon and steam are mixed and subjected to a primary reforming reaction. Then, oxygen is added, and a partial oxidation and a secondary reforming reaction are carried out. The resultant gas having a high temperature is used as a heat source for the primary reforming reaction. Advantageously, this method requires no external supply of heat, nor does it require a reforming furnace in which reaction tubes are to be externally heated. Therefore, a synthesis gas having a high pressure can be obtained, and the synthesis reaction of the synthesis gas can be directly carried out without increasing the pressure of the synthesis gas with a compressor. Thus, the reforming reaction is carried out under a high pressure, the capacity of the apparatus therefor can be easily increased.

U.S. Pat. Nos. 4,666,680, 5,112,578 and 5,156,821 disclose specific structures of self heat-exchanger type reactors in which the primary and secondary reforming reactions are carried out.

The reaction for reforming a hydrocarbon with steam is represented by the following reaction schemes.

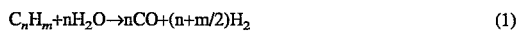

$$C_nH_m + nH_2O \rightarrow nCO + (n+m/2)H_2 \quad (1)$$

$$CO + H_2O \rightleftharpoons CO_2 + H_2 \quad (2)$$

In the development of a large-scale apparatus for the production of methanol, it is desired to improve the energy efficiency, and concerning a gas-reforming apparatus, it is under way to develop a self heat-exchanger type reactor for carrying out the primary reforming reaction and the secondary reforming reaction as described above. For an apparatus for the synthesis of methanol, the development of a fluidized bed catalyst reactor is under way as already described, while the gas flow speed is required to be 0.4 to 0.6 m/second for achieving an optimum fluidization state of a catalyst as described in U.S. Pat. No. 4,956,392. Therefore, the amount of a feed gas to a methanol synthesis reactor is defined, and it is required to decrease the amount of a circulating gas as low as possible. However, when the synthesis gas circulation ratio (amount of circulating gas/amount of synthesis gas) is decreased, the concentration of carbon oxides ($CO+CO_2$) in a gas fed to the methanol synthesis reactor increases, and the temperature in the reactor is liable to increase. As a result, the amount of byproducts such as paraffin increases, and the activity of the catalyst may decrease to a great extent.

In the self heat-exchanger type reactor in which the primary reforming reaction, partial oxidation reaction and secondary reforming reaction are carried out, mainly, hydrogen in a gas from the primary reforming reaction reacts with oxygen to increase the concentration of carbon oxides ($CO+CO_2$) in a synthesis gas. That is, the concentration of carbon oxides ($CO+CO_2$) in the synthesis gas to be fed to a methanol synthesis apparatus increases. The apparatus for the production of methanol comprises a gas-reforming apparatus having a self heat-exchanger type reactor in which the primary reforming reaction, partial oxidation and secondary reforming reaction are carried out and a methanol synthesis apparatus having a fluidized bed catalyst reactor. Therefore, special reaction conditions and improvements in the methanol synthesis process are required for developing a large-scale apparatus for the production of methanol, which apparatus has high energy efficiency.

SUMMARY OF THE INVENTION

It is an object of the present invention to provide a process for the production of methanol, which exhibits high energy efficiency and permits the production of methanol with a large-scale apparatus.

It is another object of the present invention to provide a process for the production of methanol, which accomplishes high energy efficiency and comprises a gas reforming step including the steps of primary reforming, partial oxidation and secondary reforming, and a methanol synthesis step using a fluidized bed catalyst reactor, in which the above two steps (gas reforming step and methanol synthesis step) can be carried out with apparatus of which the capacities are increased.

According to the present invention, there is provided a process for the production of methanol, comprising a primary reforming step of catalytically reacting a hydrocarbon as a raw material with steam, a partial oxidation step of partially oxidizing a gas fed from the above primary reforming reaction step by adding an oxygen gas, a secondary reforming step of catalytically reacting a gas fed from the above partial oxidation step with steam, a step of using a high-temperature gas obtained from the secondary reforming reaction step, as a heat source for the primary reforming step, a synthesis gas preparation step of separating steam from the gas used as the above heat source to prepare a synthesis gas, and a methanol synthesis step of introducing the synthesis gas into a methanol synthesis reactor using a fluid catalyst, wherein:

the molar ratio of hydrogen to carbon oxides in a feed gas to be introduced into the methanol synthesis reactor, represented by [$H_2/(2CO+3CO_2)$], is set at from 1.0 to 2.7, the molar ratio of $CO_2/CO$ in the feed gas to be introduced into the methanol synthesis reactor is set at from 0.6 to 1.2, a gas from the methanol synthesis reactor is partially introduced into the methanol synthesis reactor as a circulating gas together with the synthesis gas, and a remaining part of the gas from the methanol synthesis reactor is introduced into the gas reforming step as a purge gas together with the hydrocarbon as a raw material.

DETAILED DESCRIPTION OF THE INVENTION

Figure 1:
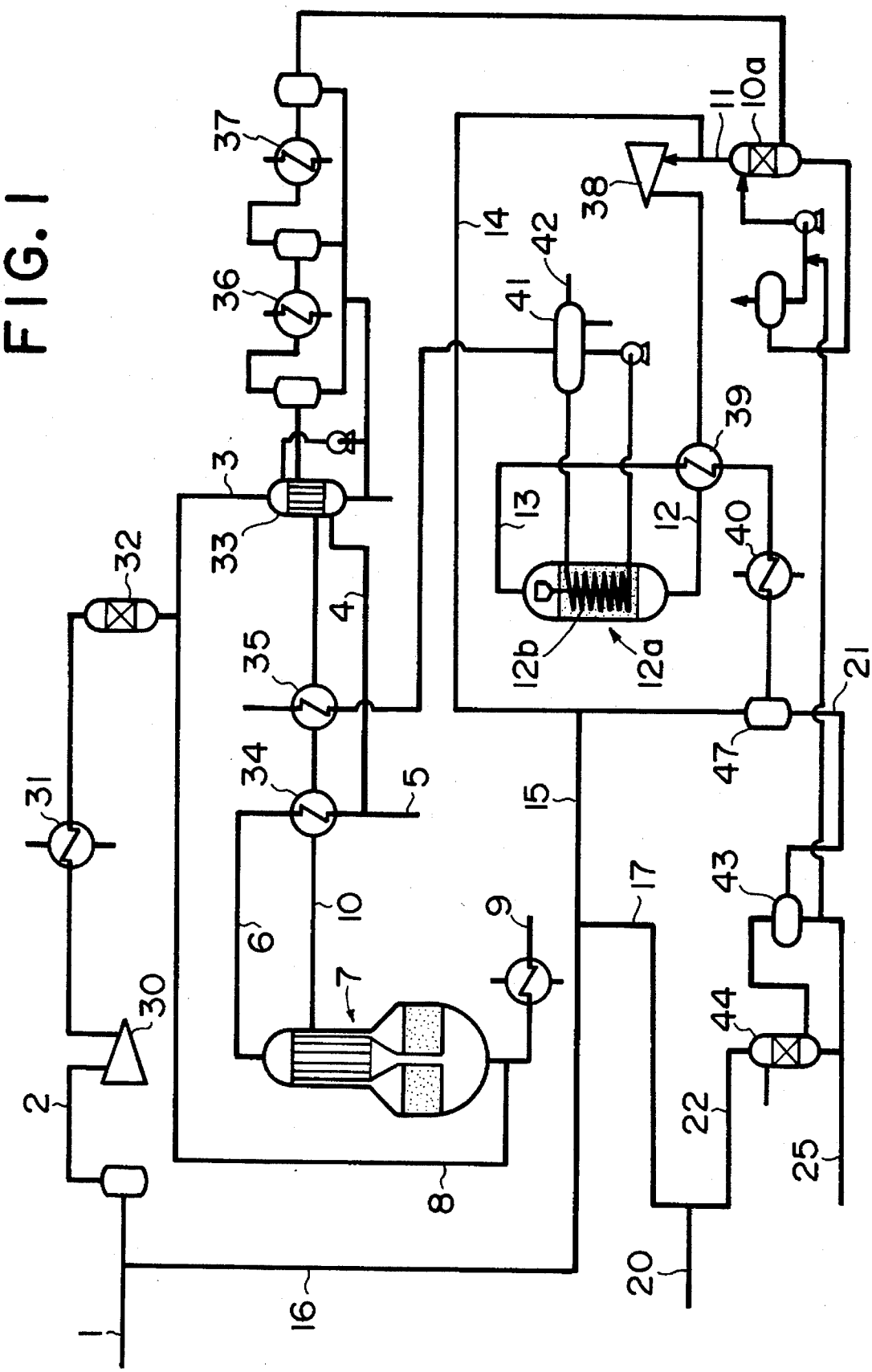
FIG. 1 is a flow chart showing the introduction of a synthesis gas prepared by removing a predetermined amount of carbon dioxide gas with crude methanol to a methanol synthesis reactor.

The present inventors have made diligent studies to overcome the above problems of an apparatus for the production of methanol, which comprises a gas reforming apparatus using a self heat-exchanger type reactor for carrying out the primary reforming reaction, partial oxidation and secondary reforming reaction and a methanol synthesis apparatus using a fluidized bed catalyst reactor. As a result, it has been found that an apparatus for the production of methanol, which can achieve high yields and a high energy efficiency and permits an increase in the capacity of the apparatus, can be obtained by defining the composition of a feed gas to a methanol synthesis reactor.

A method for accomplishing the composition of a feed gas to a methanol synthesis reactor with high energy efficiency includes the following conditions.

1) Part of purge gas from the methanol synthesis apparatus is mixed with hydrocarbon as a raw material, and 40 to 80% of the mixed gas (mixture of purge gas and hydrocarbon) is introduced into primary reforming reaction tubes after the steam/total carbon of raw material molar ratio (S/C) is adjusted to from 1.5 to 4.0. In the reaction tubes, the primary reforming reaction is carried out such that outlets of the reaction tubes show a pressure of 25 to 95 atmospheric pressures and a temperature of 700° to 800° C.

2) The resultant primary reformed gas and the remainder of the mixed gas (purge gas and hydrocarbon) are introduced into a combustion chamber together with oxygen gas in an amount of 0.40 to 0.46 mol per mole of a total carbon of the hydrocarbon as a raw material to carry out the partial oxidation and the subsequent secondary reforming reaction.

For achieving the above composition of a feed gas to the methanol synthesis reactor such that higher energy efficiency can be obtained, the following process may be employed.

1) Carbon dioxide gas is removed from a reformed gas obtained from the gas reforming step or a purge gas from the methanol synthesis step, and the remainder is introduced into the methanol synthesis reactor.

2) The heat of evaporation of liquid oxygen to be used in the gas reforming step and/or the sensible heat of a low-temperature oxygen gas to be used in the gas reforming step is used as a cooling source in the methanol synthesis step.

3) Hydrogen separated from a purge gas from the methanol synthesis step with a PSA (pressure swing adsorption) apparatus is introduced into the methanol synthesis step.

The present invention will be detailed hereinafter.

For bringing the composition of a feed gas to the methanol synthesis reactor using a fluid catalyst into the above range, various factors are to be considered, such as the composition of the synthesis gas to be introduced into the methanol synthesis step, the reaction ratio in the methanol synthesis reactor, the amount ratio of a purge gas from the methanol synthesis step, the amount ratio between the synthesis gas and the circulating gas, and the like, while the composition of the synthesis gas from the gas reforming step is the main factor which affects the composition of the feed gas.

The gas reforming step generally uses a natural gas composed mainly of methane as hydrocarbon as a raw material, while LPG and naphtha are also used in some locations. Further, for improving the unit requirement of the raw material, a purge gas from the methanol synthesis step is also used together with the hydrocarbon. A nickel-containing catalyst is generally used as a steam reforming catalyst, and for avoiding the deactivation of the catalyst, it is required to desulfurize the hydrocarbon as a raw material in advance.

In the present invention, for bringing the composition of a feed gas to the methanol synthesis reactor into the above range such that higher energy efficiency can be obtained, part of a purge gas from the methanol synthesis step is mixed with hydrocarbon as a raw material, and 40 to 80% of the mixed gas is introduced into the primary reforming reaction tubes after the steam/total carbon of raw material molar ratio (S/C) is adjusted to from 1.5 to 4.0. This mixed gas to be introduced into the primary reforming reaction tubes is preferably heated to about 400° to 550° C.

When the amount of mixed gas (mixture of purge gas and hydrocarbon) which bypasses (i.e., the amount of mixed gas fed to the partial oxidation) is too large, the amounts of hydrocarbon as a raw material and steam used in the primary reforming reaction are small, and the amount of hydrogen generated is small. As a result, the stoichiometric ratio between hydrogen and carbon oxides in the feed gas to the methanol synthesis reactor decreases, and the amount of oxygen used for the partial oxidation increases. In the present specification, the "stoichiometric ratio" refers to a [$H_2/(2CO+3CO_2)$] molar ratio in the feed gas to the methanol synthesis reactor.

When the amount of mixed gas which bypasses is too small, the amount of mixed gas to be fed to the primary reforming reaction is large, and the amounts of hydrocarbon as a raw material and steam are large. As a result, the $CO_2/CO$ molar ratio (to be referred to as "$CO_2$ ratio"

hereinafter) in the feed gas to the methanol synthesis reactor increases.

In the steam reforming reaction, the mixed gas of hydrocarbon and steam is indirectly heated through primary reforming reaction tubes to carry out a primary reforming catalytic reaction, such that the outlets of the primary reforming reaction tubes show a pressure of 25 to 95 atmospheric pressures and a temperature of 700° to 800° C. The primary reformed gas and a remainder of the mixed gas (of purge gas and hydrocarbon as a raw material) are introduced into a combustion chamber together with an oxygen gas in an amount of 0.40 to 0.46 mol per mole of total carbon of the hydrocarbon as a raw material to carry out a partial oxidation reaction and a subsequent secondary reforming reaction. The resultant, high-temperature, reformed gas is subjected to various heat recoveries, and then cooled to form a synthesis gas containing, as effective components, hydrogen, carbon monoxide and carbon dioxide gas.

The primary reformed gas is partially oxidized and then subjected to the secondary reforming reaction. As a result, the pressure in the gas reforming apparatus is increased, and the power required for a compressor compressing the synthesis gas can be decreased. Therefore, the energy efficiency in the methanol process can be improved. Further, the size of the gas reforming apparatus can be decreased since it can be operated at an increased pressure, and the decreased size of the gas reforming apparatus is advantageous for increasing the capacity of the methanol production apparatus.

Further, when the secondary reformed gas is used as a heat source for the primary reforming reaction, the difference between the pressure inside the primary reforming reaction tubes and the pressure of the heating gas is small. As a result, a heat-exchanger type reactor can be used, and no externally heated reforming furnace is required. Therefore, a gas reforming apparatus operable at a higher pressure can be employed, and at the same time, it is also facile to cope with an increase in the capacity of the apparatus. Further, when the pressure of the gas reforming apparatus is properly arranged to be higher than the pressure of the methanol synthesis apparatus, no compressor for the synthesis gas is required.

A fluidized bed catalyst reactor is used as the methanol synthesis reactor, in which methanol is synthesized from hydrogen, carbon monoxide and carbon dioxide gas according to the following reaction schemes.

$$CO + 2H_2 \rightarrow CH_3OH + 21.6 \text{ kcal/mol}$$

$$CO_2 + H_2 \rightarrow CO + H_2O - 9.8 \text{ kcal/mol}$$

$$CO_2 + 3H_2 \rightarrow CH_3OH + H_2O + 11.8 \text{ kcal/mol}$$

Generally, a copper-containing catalyst is used for the methanol synthesis reaction, and the reaction is carried out at a temperature of 200° to 300° C. at a pressure of 60 to 120 atmospheric pressures.

As a fluid catalyst for the methanol synthesis, generally, there is used a catalyst prepared by allowing a solid support such as silica, alumina or zirconium to support the catalyst component, and the catalyst has a particle diameter of 1 to 250 μm.

The methanol synthesis uses a fluidized bed catalytic reactor having heat-transfer tubes inside, and the heat of reaction is transmitted to saturated water through the heat-transfer tubes, whereby high-pressure steam having a pressure of 20 to 60 atmospheric pressures, preferably 25 to 55 atmospheric pressures, is recovered.

The high-pressure steam obtained may be used as a steam for the gas reforming step, while it can improve the energy efficiency of the methanol production process when used as a power source for a synthesis gas compressor, a synthesis gas circulator or a compressor for hydrocarbon gas as a raw material.

An oxygen separating apparatus for preparation of oxygen for the partial oxidation uses a cryogenic separation method, and the oxygen gas used for the partial oxidation generally has a purity of at least 98%. When liquid oxygen is introduced into the gas reforming step, the heat of evaporation thereof and the sensible heat of low-temperature oxygen gas are used as a cooling source for the methanol synthesis step, i.e., a cooling source used in a condenser for separating crude methanol, so that the energy efficiency of the methanol production step can be improved.

In the present invention, the stoichiometric ratio of hydrogen to carbon oxides $[H_2/(2CO+3CO_2)]$ in the feed gas to the methanol synthesis reactor is 1.0 to 2.7, preferably 1.1 to 2.0, more preferably 1.2 to 1.8. When the above stoichiometric ratio is lower than 1.0, the yield of methanol relative to carbon oxides $(CO+CO_2)$ [to be referred to as "$(CO+CO_2)$ yield" hereinafter] is low. When it is higher than 2.7, the volume productivity of methanol is low.

U.S. Pat. No. 4,782,096 describes a process for the production of methanol using a synthesis gas having a stoichiometric ratio of hydrogen to carbon dioxide $(H_2/(2CO+3CO_2))$ of 1.0 or less, prepared by adding a hydrogen-enriching gas to a synthesis gas.

Conventionally, the optimum stoichiometric ratio of the composition of a gas to be fed to a methanol synthesis reactor is considered to be 1.0. In the present invention, however, it has been found, after detailed studies of the relationship between the productivity and yield of methanol using a fluidized bed catalyst reactor, that the optimum stoichiometric ratio in a practical apparatus is greater than 1.0. Further, the optimum stoichiometric ratio also differs depending upon the $CO_2$ ratio ($CO_2/CO$ molar ratio) of a feed gas to the reactor. For example, when the $CO_2$ ratio is 1.2, the optimum stoichiometric ratio is 1.7 to 2.1, and when the $CO_2$ ratio is 0.6, the optimum stoichiometric ratio is 1.0 to 2.7.

In the present invention, the $CO_2$ ratio of the feed gas to the methanol synthesis reactor using a fluidized bed catalyst reactor is 0.6 to 1.2, preferably 0.6 to 1.0. When the $CO_2$ ratio is too low, the temperature in the reactor is liable to increase, and the amount of byproducts such as paraffin may increase. Further, the catalyst may be greatly deactivated. When the $CO_2$ ratio is too high, the yield of methanol relative to $(CO+CO_2)$ decreases, and the amount of formed $H_2O$ increases. Thus, the catalyst is also liable to be deactivated.

In the self heat-exchanger type reactor for carrying out the primary reforming, partial oxidation and secondary reforming, hydrogen is consumed by partial oxidation as described already, and therefore, the stoichiometric ratio of hydrogen to carbon oxides in the feed gas to the methanol synthesis reactor decreases. Further, with an increase in the amount of hydrocarbon having 2 or more carbon atoms contained in the hydrocarbon as a raw material, the stoichiometric ratio further decreases. How to cope with such a decrease in the stoichiometric ratio will be explained below.

In order to cope with a decrease in the stoichiometric ratio, first, carbon dioxide gas is removed from the synthesis gas. Carbon dioxide gas can be removed by various methods. For example, crude methanol obtained in the methanol synthesis step may be used as a liquid for absorbing the carbon dioxide gas. The crude methanol may be cooled by means of the heat of evaporation of liquid oxygen to be used in the gas reforming step and the sensible heat of low-temperature oxygen gas to be used in the gas reforming step.

Further, the heat of evaporation of liquid oxygen to be used in the gas reforming step and the sensible heat of low-temperature oxygen gas to be used in the gas reforming step may be also used as a cooling source for a condenser used for separating crude methanol, and when the temperature for cooling the crude methanol is decreased, the amount of dissolved $CO_2$ increases. As a result, the stoichiometric ratio in the feed gas to the methanol synthesis reactor increases, and the $CO_2$ ratio is decreases. Therefore, there is obtained a gas composition more preferable for the fluidized bed catalyst reactor.

In order to cope with a decrease in the stoichiometric ratio, there is another method in which carbon dioxide gas is removed from a purge gas from the methanol synthesis step and the resultant purge gas is fed to the methanol synthesis step. In this case, the carbon dioxide can be also removed by the above method. In addition, when carbon dioxide gas is removed as above, the $CO_2$ ratio in the feed gas to the methanol synthesis reactor is decreased, and it is therefore necessary to control the $CO_2$ ratio.

In order to cope with a decrease in the stoichiometric ratio, there is further another method in which hydrogen is recovered from a purge gas of the methanol synthesis step and fed to the methanol synthesis reactor. In this case, a PSA (pressure swing adsorption) apparatus is used for recovering hydrogen. A purge gas from the methanol synthesis step or a waste gas from the PSA apparatus has been used as a fuel for a reforming furnace of a conventional steam reforming apparatus, while it is used as a fuel for a gas turbine engine in the present invention since the process of the present invention requires no reforming furnace.

Further, when the high-pressure steam recovered from the methanol synthesis reactor is heated with waste heat from the gas turbine engine and used as a power source, higher energy efficiency can be obtained.

FIGS. 1 to 4 show flow charts of processes for the production of methanol, employing the gas reforming step and the methanol synthesis step used in the present invention.

FIG. 1 shows an embodiment in which methanol is produced by removing a predetermined amount of carbon dioxide gas from the synthesis gas obtained from the gas reforming step with crude methanol and then introducing the remaining synthesis gas into the methanol synthesis reactor.

In FIG. 1, hydrocarbon as a raw material from a flow path 1 and a purge gas (from a methanol synthesis step) from a flow path 16 is mixed, and the mixed gas is passed through a flow path 2. The mixed gas is pressurized with a compressor 30, heated with a heat exchanger 31, and desulfurized with a desulfurizer 32. Then, part of the mixed gas is passed through a flow path 3, heated with a heater 33, then passed through a flow path 4, combined with process steam from a flow path 5, heated with a heat exchanger 34 and then introduced into a gas reforming reactor 7 through a flow path 6.

A primary reforming reaction takes place in an upper portion of the gas reforming reactor 7. Then, a remainder of the mixed gas (hydrocarbon and purge gas), which is passed through a flow path 8, is introduced into a lower portion of the gas reforming reactor 7 together with oxygen from a flow path 9, and a partial oxidation is carried out. Then, a secondary reforming reaction takes place, and then, a reformed gas is recovered through a flow path 10. The secondary reformed gas heats primary reforming reaction tubes.

The reformed gas is used for heat recovery in the heat exchangers 34 and 35, the heater 33 and a heat exchanger 36, and then cooled with a condenser 37 to condense and separate unreacted steam. As a result, a synthesis gas is obtained. A predetermined amount of carbon dioxide gas is removed from the synthesis gas with crude methanol in a carbon dioxide absorption column 10a. Crude methanol cooled using the heat of evaporation of liquid oxygen, etc., is advantageously used as a crude methanol, since the amount of carbon dioxide gas which can be dissolved in the crude methanol increases. The synthesis gas from which carbon dioxide gas has been removed is passed through a flow path 11, pressurized with a compressor 38 which also works as a synthesis gas circulating device, heated with a heat exchanger 39, passed through a flow path 12 and then fed into a fluidized bed catalyst reactor 12a for the synthesis of methanol. The heat of reaction is transmitted to water inside heat-transfer tubes 12b placed inside the reactor 12a, and high-pressure steam is recovered from a separator 41. In FIG. 1, the high-pressure steam is reheated with the heat exchanger 35. This high-pressure steam can be widely used as the process steam from the flow path 5 and a power source for compressors. Water is fed through a flow path 42, and boiler water is suitable for use.

Upstream of the compressor 38 and in the flow path 11, the synthesis gas is combined with a circulating gas branched from a gas from the reactor 12a through a flow path 14. In the reactor 12a, a methanol synthesis reaction takes place. A reaction gas from the reactor 12a is subjected to heat recovery with the heat exchanger 39, cooled with a condenser 40, and separated into crude methanol and gas with a high-pressure separator 47. Part of the gas is used as a circulating gas passing through the flow path 14, and another part thereof is passed, as a purge gas, through flow paths 15 and 16 and combined with hydrocarbon as a raw material. A remainder of the purge gas is passed through flow paths 17 and 20, and used as a fuel for a gas turbine engine (not shown). The crude methanol is introduced into a low-pressure separator 43 through a flow path 21, and separated into crude methanol and a dissolved gas. Further, the dissolved gas is washed with water through a washing column 44 to separate methanol from the dissolved gas. The separated crude methanol for a high-pressure separator 47 is combined with the crude methanol from the low-pressure separator 43 and introduced into a methanol purification apparatus through a flow path 25. The dissolved gas which has been separated is passed through flow paths 22 and 20 and used as a fuel for a gas turbine engine.

Figure 2:
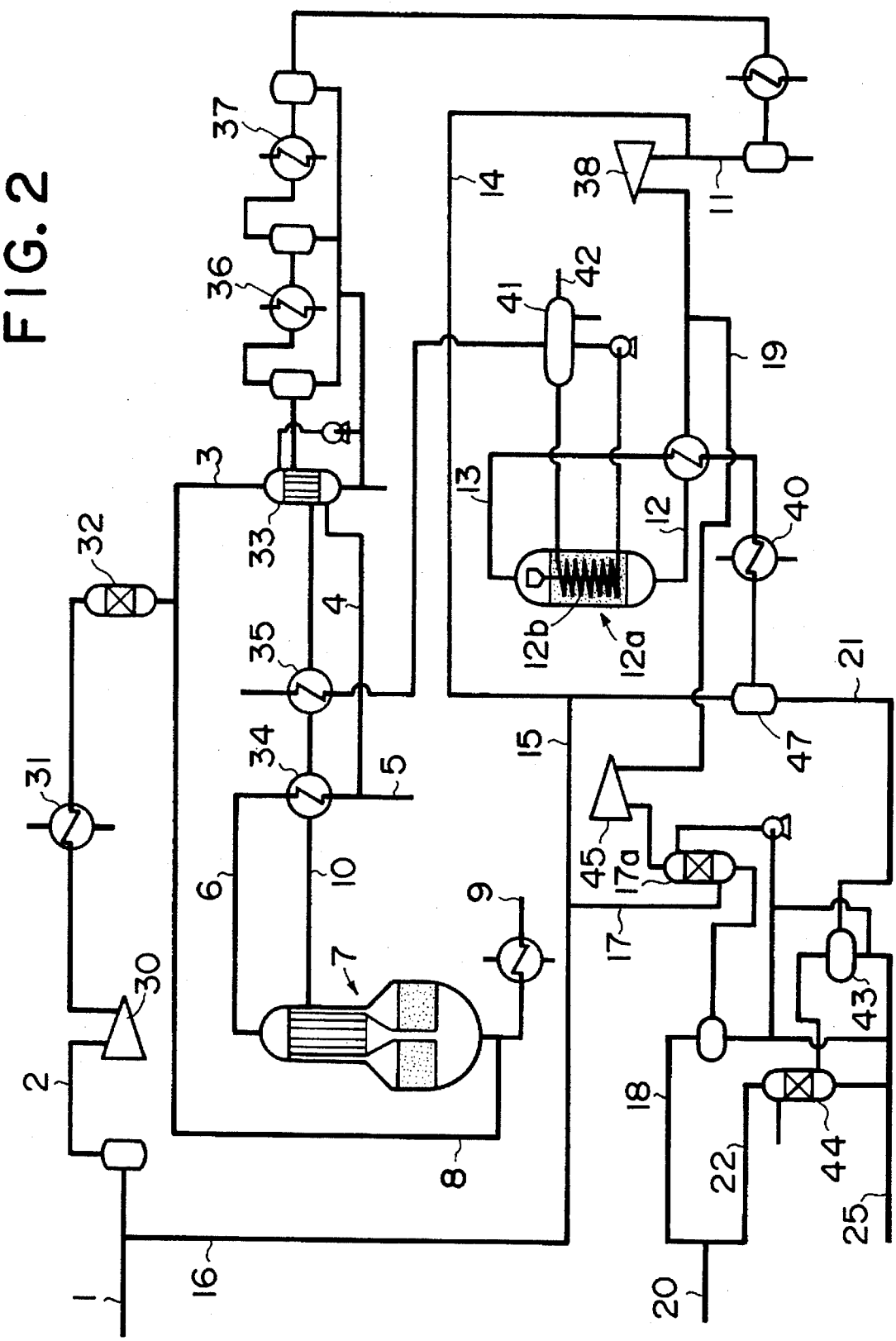
FIG. 2 is a flow chart showing the introduction of a purge gas prepared by removing a predetermined amount of carbon dioxide gas with crude methanol to a methanol synthesis reactor.

FIG. 2 shows a modified embodiment in which methanol is produced by removing a predetermined amount of carbon dioxide gas from part of purge gas from the methanol synthesis step, and then introducing the resultant part of purge gas into a reactor 12a together with a synthesis gas.

In FIG. 2, a purge gas is passed through flow paths 15 and 17, and then in a carbon dioxide absorption column 17a, crude methanol absorbs carbon dioxide gas to remove it from the purge gas. Crude methanol cooled to a low temperature is advantageous as such, since the amount of dissolved carbon dioxide gas increases. The purge gas from which carbon dioxide gas has been removed is pressurized with a compressor 45, passed through a flow path 19, combined with a synthesis gas from a flow path 11 downstream of a compressor 38, and introduced into a reactor 12a.

Figure 3:
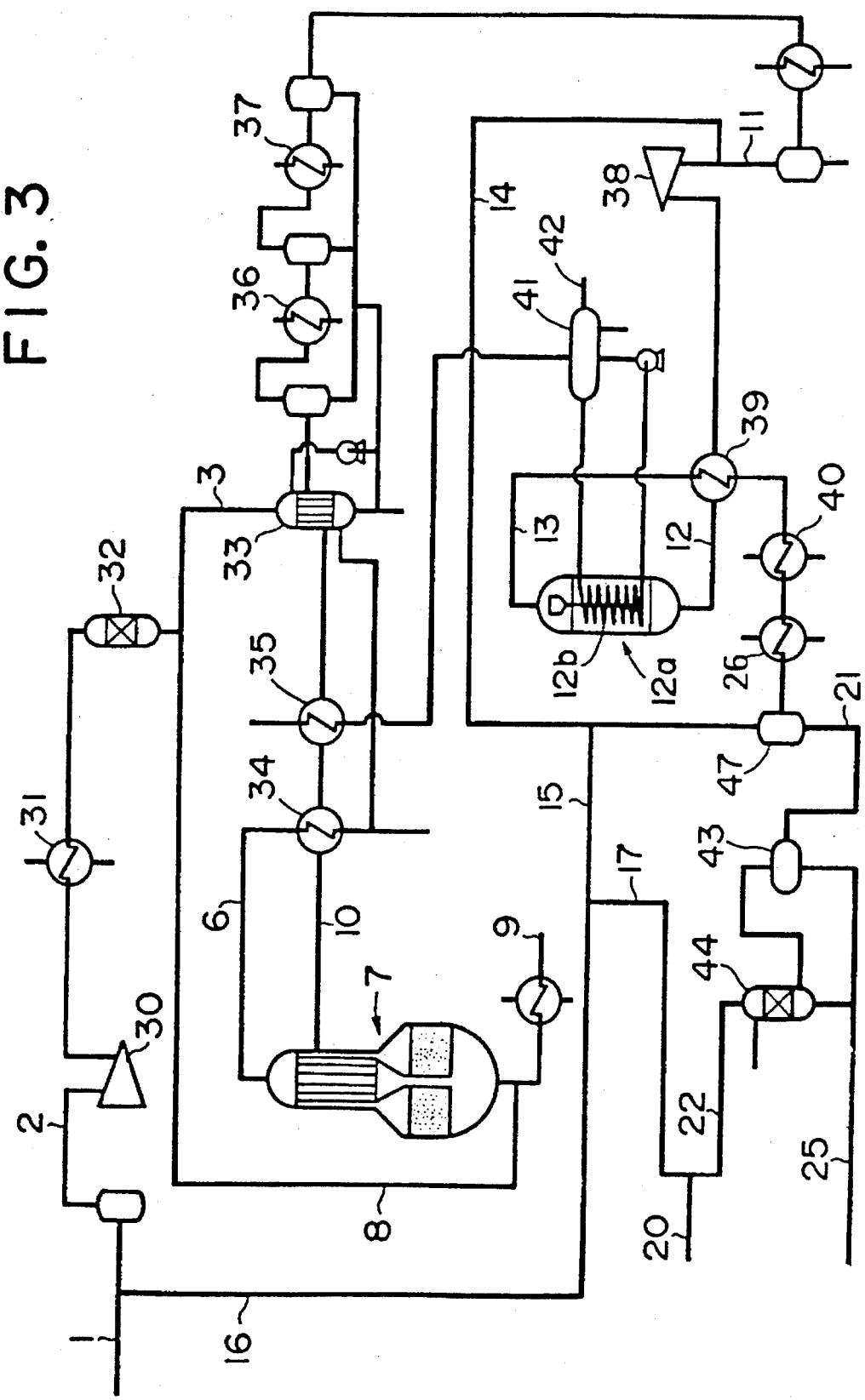
FIG. 3 is a flow chart showing the introduction of a gas portion, which is separated from a gas from a methanol synthesis reactor by cooling the gas with the heat of evaporation of liquid oxygen to be used in a gas reforming step and the sensible heat of a low-temperature oxygen gas to be used in the gas reforming step, to a methanol synthesis reactor as a circulating gas together with a synthesis gas.

FIG. 3 shows a modified embodiment in which a gas from a fluid catalyst reactor 12a is cooled by the heat of evaporation of liquid oxygen to be used in the gas reforming step and the sensible heat of low-temperature oxygen to be used in the gas reforming step, and a separated gas portion is fed to the reactor 12a as a circulating gas together with the synthesis gas.

The reaction gas from the fluid catalyst reactor 12a is subjected to heat recovery with a heat exchanger 39, cooled with a condenser 40 and cooled with a crude methanol condenser 26 to be separated into crude methanol and gas. The crude methanol condenser 26 uses the heat of evaporation of liquid oxygen and the sensible heat of low-temperature oxygen gas for cooling the reaction gas, so that the crude methanol can be cooled to a very low temperature, and the amount of carbon dioxide gas which can be dissolved in methanol can be remarkably increased.

Figure 4:
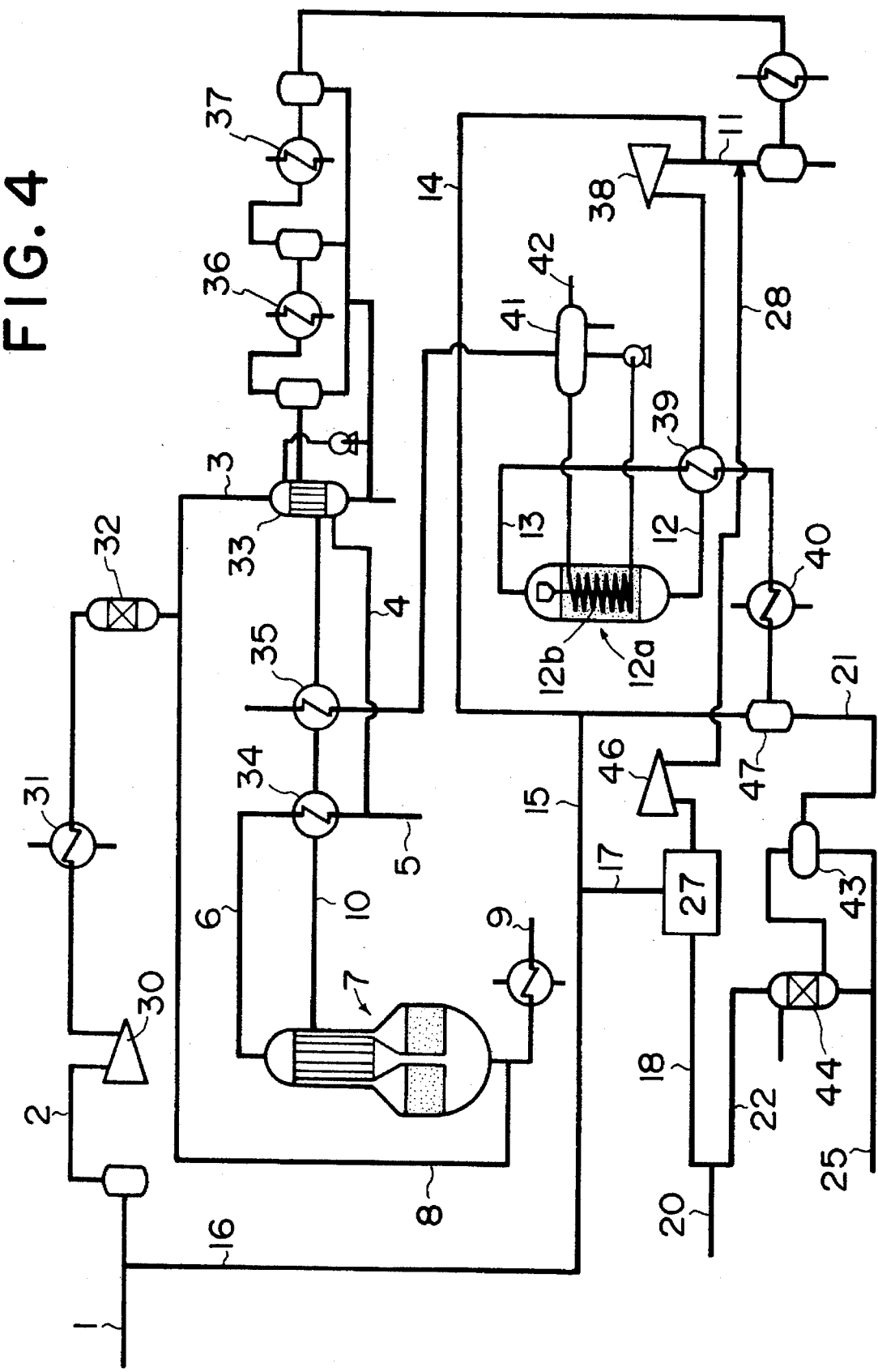
FIG. 4 is a flow chart showing the introduction of hydrogen separated from part of a purge gas with a pressure swing adsorption (PSA) apparatus to a methanol synthesis reactor.

FIG. 4 shows a modified embodiment in which hydrogen is separated from part of a purge gas obtained from the methanol synthesis step with a pressure swing method adsorption (PSA) apparatus, and the separated hydrogen is introduced into a reactor 12a to produce methanol.

A purge gas from a flow path 17 is introduced into a PSA apparatus 27 to separate hydrogen, and the separated hydrogen is pressurized with a compressor 46, passed through a flow path 28, combined with a synthesis gas upstream of a compressor 38 and introduced into the reactor 12a. The purge gas from which hydrogen has been separated is passed through flow paths 18 and 20, and used as a fuel for a gas turbine engine.

The present invention will be explained more in detail hereinafter with reference to Examples. However, the present invention shall not be limited to these Examples.

Examples 1–2 and Comparative Examples 1–2

Methanol was synthesized by means of a methanol synthesis test apparatus having a fluidized bed catalyst reactor having an internal diameter of 0.31 m and a height of 20 m. A Cu—Zn—Zr—Al catalyst (average particle diameter 60 μm, particle density 2.39 g/cm$^3$) was used as a fluid catalyst. The reactor inlet gas temperature and pressure were set at 200° C. 80.0 kg/cm$^2$G, SV=9,310 (l/h), LV=0.51 m/sec, the boiler water temperature was set at 230° C., and the circulation ratio (circulating gas/synthesis gas) was set at 3.0. Under these conditions, mixed gases having various compositions were respectively reacted. Table 1 shows the results.

TABLE 1

|  | Ex. 1 | Ex. 2 | CEx. 1 | CEx. 2 |
|---|---|---|---|---|
| Composition of synthesis gas (vol %) |  |  |  |  |
| CO | 19.28 | 26.00 | 20.00 | 10.79 |
| CO$_2$ | 9.64 | 5.21 | 10.85 | 10.79 |
| H$_2$ | 68.15 | 65.86 | 66.22 | 75.50 |
| CH$_4$ | 2.39 | 2.39 | 2.39 | 2.39 |
| N$_2$ | 0.45 | 0.45 | 0.45 | 0.45 |
| H$_2$O | 0.09 | 0.09 | 0.09 | 0.09 |
| Composition of gas in reactor inlet (vol %) |  |  |  |  |
| CO | 7.57 | 11.68 | 9.38 | 4.07 |
| CO$_2$ | 9.16 | 8.48 | 16.94 | 5.32 |
| H$_2$ | 61.97 | 52.37 | 49.99 | 82.70 |
| CH4 | 17.36 | 22.42 | 19.32 | 6.25 |
| N$_2$ | 3.48 | 4.63 | 3.91 | 1.19 |
| H$_2$O | 0.04 | 0.03 | 0.04 | 0.05 |
| CH$_3$OH | 0.42 | 0.42 | 0.42 | 0.42 |
| Stoichiometricratio | 1.46 | 1.08 | 0.72 | 3.43 |
| CO$_2$ ratio | 1.21 | 0.73 | 1.81 | 1.31 |
| Yield based on CO + CO$_2$ (%) | 92.7 | 93.0 | 87.5 | 90.3 |
| Methanol production (ton/day) | 10.2 | 11.1 | 10.3 | 7.4 |

Example 3

According to the flow shown in FIG. 1, carbon dioxide gas was removed from a gas prepared with a gas reforming apparatus, and the resultant gas was introduced into a synthesis apparatus to produce methanol.

The main reaction conditions in the gas reforming apparatus and the methanol synthesis apparatus were as follows.

Primary reforming inlet temperature 500° C.

Primary reforming inlet pressure 83.0 kg/cm$^2$G

Primary reforming outlet temperature 790° C.

Secondary reforming outlet temperature 1,030° C.

Reforming reactor outlet temperature 551° C.

Reforming reactor outlet pressure 79.7 kg/cm$^2$G

Methanol synthesis reactor inlet temperature 198° C.

Methanol synthesis reactor outlet temperature 263° C.

Methanol synthesis reactor pressure 80.0 kg/cm$^2$G

Stoichiometric ratio in methanol synthesis reactor inlet 1.67

CO$_2$ ratio in methanol synthesis reactor inlet 0.997

Yield based on CO+CO$_2$ 93.3%

Tables 2 to 6 show flow amounts and compositions in main portions in the case of the production of 5,000 tons/day of methanol. In Tables 2 to 6, values for CH$_3$OH include values of byproduct. As a result, there was obtained a methanol process achieving an energy unit consumption of 6.948 MMkcal per ton of purified methanol.

TABLE 2

| Hydrocarbons as raw material | Flow division (1) (flow path 3) (kg-mol/h) | Flow division (2) (flow path 8) (kg-mol/h) | Composition (mol %) |
|---|---|---|---|
| CH$_4$ | 3,250.4 | 2,167.1 | 78.68 |
| C$_2$H$_6$ | 270.8 | 180.5 | 6.55 |
| C$_3$H$_8$ | 105.2 | 70.2 | 2.55 |
| C$_4$H$_{10}$ | 48.2 | 32.1 | 1.17 |
| C$_5$H$_{12}$ | 16.4 | 10.9 | 0.40 |
| C$_6$H$_{14}$ | 5.5 | 3.8 | 0.14 |
| CO | 19.7 | 13.2 | 0.48 |
| CO$_2$ | 56.0 | 37.3 | 1.36 |
| H$_2$ | 330.5 | 220.4 | 8.00 |
| N$_2$ | 24.8 | 16.5 | 0.60 |
| H$_2$O | 0.2 | 0.1 | 0.00 |
| CH$_3$OH | 3.0 | 2.0 | 0.07 |
| Total | 4,130.7 | 2,754.1 | 100.00 |

TABLE 3

Steam as raw material (flow path 5) 12,846.8 kg-mol/h
Oxygen gas (flow path 9)

| O$_2$ | 3,015.2 kg-mol/h | 99.50 mol % |
|---|---|---|
| N$_2$ | 15.2 | 0.50 |
| Total | 3,030.4 | 100.00 |

TABLE 4

|  | Secondary reforming outlet gas (flow path 10) | | Synthesis gas (flow path 11) | |
|---|---|---|---|---|
|  | kg-mol/h | mol % | kg-mol/h | mol % |
| CH$_4$ | 555.9 | 1.53 | 511.9 | 2.21 |
| CO$_2$ | 2,132.8 | 5.86 | 1,994.3 | 8.62 |
| CO | 4,806.4 | 13.20 | 4,780.7 | 20.67 |
| H$_2$ | 15,783.6 | 43.33 | 15,751.8 | 68.11 |
| N$_2$ | 56.5 | 0.16 | 56.0 | 0.24 |

TABLE 4-continued

| | Secondary reforming outlet gas (flow path 10) | | Synthesis gas (flow path 11) | |
|---|---|---|---|---|
| | kg-mol/h | mol % | kg-mol/h | mol % |
| $H_2O$ | 13,086.3 | 35.92 | 4.9 | 0.02 |
| $CH_3OH$ | | | 30.4 | 0.13 |
| Total | 36,421.5 | 100.00 | 23,130.0 | 100.00 |

TABLE 5

| | Synthesis reactor inlet gas (flow path 12) | | Outlet gas (flow path 13) | |
|---|---|---|---|---|
| | kg-mol/h | mol % | kg-mol/h | mol % |
| $CH_4$ | 22,426.1 | 21.42 | 22,426.1 | 24.45 |
| $CO_2$ | 7,618.9 | 7.28 | 5,841.1 | 6.37 |
| CO | 7,638.1 | 7.29 | 2,922.2 | 3.19 |
| $H_2$ | 63,600.0 | 60.73 | 48,835.0 | 53.22 |
| $N_2$ | 2,923.7 | 2.79 | 2,923.7 | 3.19 |
| $H_2O$ | 36.7 | 0.04 | 1,820.9 | 1.99 |
| $CH_3OH$ | 468.3 | 0.45 | 6,955.5 | 7.59 |
| Total | 104,711.8 | 100.00 | 91,724.5 | 100.00 |

TABLE 6

| | Circulating gas (flow path 14) | | Crude methanol (flow path 25) | |
|---|---|---|---|---|
| | kg-mol/h | mol % | kg-mol/h | mol % |
| $CH_4$ | 21,917.7 | 26.87 | 0.9 | 0.01 |
| $CO_2$ | 5,624.5 | 6.89 | 18.9 | 0.22 |
| CO | 2,857.4 | 3.50 | 0.1 | 0.00 |
| $H_2$ | 47,850.3 | 58.65 | 0.0 | 0.00 |
| $N_2$ | 2,864.1 | 3.51 | 0.0 | 0.00 |
| $H_2O$ | 31.8 | 0.04 | 2,198.4 | 25.19 |
| $CH_3OH$ | 438.0 | 0.54 | 6,507.3 | 74.57 |
| Total | 81,583.8 | 100.00 | 8,725.6 | 100.00 |

Amount of purge gas
(flow path 15) 1,615.04 kg-mol/h
(flow path 16) 939.27 kg-mol/h

Example 4

According to the flow shown in FIG. 2, carbon dioxide gas was removed from part of a purge gas from a methanol synthesis apparatus with crude methanol, and the resultant gas was introduced into a synthesis apparatus to produce methanol.

The main reaction conditions in the gas reforming apparatus and the methanol synthesis apparatus were as follows.

Primary reforming inlet temperature 500° C.
Primary reforming inlet pressure 83.0 kg/cm²G
Primary reforming outlet temperature 790° C.
Secondary reforming outlet temperature 1,030° C.
Reforming reactor outlet temperature 564° C.
Reforming reactor outlet pressure 79.7 kg/cm²G
Methanol synthesis reactor inlet temperature 198° C.
Methanol synthesis reactor outlet temperature 263° C.
Methanol synthesis reforming reactor pressure 80.0 kg/cm²G Stoichiometric ratio in methanol synthesis reactor inlet 1.27

$CO_2$ ratio in methanol synthesis reactor inlet 1.08

Yield based on $CO+CO_2$ 94.5%

Tables 7 to 11 show flow amounts and compositions in main portions in the case of the production of 5,000 ton/day of methanol. In Tables 7 to 11, values for $CH_3OH$ include values of byproduct. As a result, there was obtained a methanol process achieving an energy unit consumption of 6.930 MMkcal per ton of purified methanol.

TABLE 7

| Gas reforming apparatus | Flow division (1) (flow path 3) (kg-mol/h) | Flow division (2) (flow path 8) (kg-mol/h) | Composition (mol %) |
|---|---|---|---|
| $CH_4$ | 3,306.2 | 2,208.0 | 79.43 |
| $C_2H_6$ | 267.2 | 178.4 | 6.42 |
| $C_3H_8$ | 103.9 | 69.3 | 2.50 |
| $C_4H_{10}$ | 47.6 | 31.7 | 1.14 |
| $C_5H_{12}$ | 16.2 | 10.8 | 0.39 |
| $C_6H_{14}$ | 5.6 | 3.8 | 0.14 |
| CO | 28.2 | 18.8 | 0.68 |
| $CO_2$ | 67.6 | 45.2 | 1.62 |
| $H_2$ | 289.6 | 193.4 | 6.96 |
| $N_2$ | 25.8 | 17.3 | 0.62 |
| $H_2O$ | 0.2 | 0.2 | 0.01 |
| $CH_3OH$ | 3.6 | 2.4 | 0.09 |
| Total | 4,161.7 | 2,779.3 | 100.00 |

TABLE 8

Steam as raw material (flow path 5) 10,520.8 kg-mol/h
Oxygen gas (flow path 9)

| | | |
|---|---|---|
| $O_2$ | 3,013.5 kg-mol/h | 99.50 mol % |
| $N_2$ | 15.1 | 0.50 |
| Total | 3,028.6 | 100 |

TABLE 9

| | Secondary reforming outlet gas (flow path 10) | | Synthesis gas (flow path 11) | |
|---|---|---|---|---|
| | kg-mol/h | mol % | kg-mol/h | mol % |
| $CH_4$ | 721.5 | 2.13 | 721.5 | 3.15 |
| $CO_2$ | 1,907.7 | 5.64 | 1,907.7 | 8.32 |
| CO | 4,980.6 | 14.73 | 4,980.6 | 21.72 |
| $H_2$ | 15,235.2 | 45.06 | 15,235.2 | 66.45 |
| $N_2$ | 58.2 | 0.17 | 58.2 | 0.25 |
| $H_2O$ | 10,907.7 | 32.26 | 26.0 | 0.11 |
| Total | 33,810.9 | 100.00 | 22,929.2 | 100.00 |

TABLE 10

| | Synthesis reactor inlet gas (flow path 12) | | Outlet gas (flow path 13) | |
|---|---|---|---|---|
| | kg-mol/h | mol % | kg-mol/h | mol % |
| $CH_4$ | 43,214.6 | 32.53 | 43,214.6 | 36.08 |
| $CO_2$ | 10,546.8 | 7.94 | 8,922.5 | 7.45 |
| CO | 9,803.4 | 7.38 | 4,894.2 | 4.09 |
| $H_2$ | 64,955.6 | 48.89 | 50,263.7 | 41.96 |
| $N_2$ | 3,635.2 | 2.74 | 3,635.2 | 3.03 |
| $H_2O$ | 69.4 | 0.05 | 1,706.7 | 1.42 |

TABLE 10-continued

|  | Synthesis reactor inlet gas (flow path 12) | | Outlet gas (flow path 13) | |
| --- | --- | --- | --- | --- |
|  | kg-mol/h | mol % | kg-mol/h | mol % |
| $CH_3OH$ | 626.5 | 0.48 | 7,146.9 | 5.97 |
| Total | 132,851.5 | 100.00 | 119,783.8 | 100.00 |

TABLE 11

|  | Circulating gas (flow path 14) | | Crude methanol (flow path 25) | |
| --- | --- | --- | --- | --- |
|  | kg-mol/h | mol % | kg-mol/h | mol % |
| $CH_4$ | 42,273.5 | 38.72 | 7.1 | 0.08 |
| $CO_2$ | 8,628.8 | 7.90 | 35.7 | 0.41 |
| CO | 4,789.4 | 4.39 | 0.6 | 0.01 |
| $H_2$ | 49,268.0 | 45.13 | 0.4 | 0.00 |
| $N_2$ | 3,562.5 | 3.26 | 0.0 | 0.00 |
| $H_2O$ | 40.1 | 0.04 | 2,077.5 | 24.07 |
| $CH_3OH$ | 612.9 | 0.56 | 6,509.7 | 75.43 |
| Total | 109,175.2 | 100.00 | 8,631.0 | 100.00 |

Amount of purge gas
(flow path 15) 2,140.80 kg-mol/h
(flow path 16) 1,070.40 kg-mol/h

Example 5

According to the flow shown in FIG. 3, the heat of evaporation of liquid oxygen used in the gas reforming step and the sensible heat of low-temperature oxygen were used as a cooling source in the methanol synthesis apparatus to produce methanol.

In FIG. 3, a crude methanol condensor 26 using the heat of evaporation of liquid oxygen and the sensible heat of low-temperature oxygen was placed before a crude methanol high-pressure separator.

The main reaction conditions in the gas reforming apparatus and the methanol synthesis apparatus were as follows.

Primary reforming inlet temperature 500° C.
Primary reforming inlet pressure 83.0 kg/cm²G
Primary reforming outlet temperature 790° C.
Secondary reforming outlet temperature 1,030° C.
Reforming reactor outlet temperature 564° C.
Reforming reactor outlet pressure 79.7 kg/cm²G
Methanol synthesis reactor inlet temperature 198° C.
Methanol synthesis reactor outlet temperature 263° C.
Methanol synthesis reactor pressure 80.0 kg/cm²G
Stoichiometric ratio in methanol synthesis reactor inlet 1.39
$CO_2$ ratio 1.12
Yield based on $CO+CO_2$ 94.0%.

Tables 12 to 16 show flow amounts and compositions in main portions in the case of the production of 5,000 ton/day of methanol. In Tables 12 to 16, values for $CH_3OH$ include values of byproduct. As a result, there was obtained a methanol process achieving an energy consumption unit of 6.917 MMkcal per ton of purified methanol.

In addition, when the heat of evaporation of liquid oxygen and the sensible heat of low-temperature oxygen gas were not used in the above process, the stoichiometric ratio in methanol synthesis reactor inlet was 1.07, the $CO_2$ ratio was 1.31, the yield based on $CO+CO_2$ was 94.0%, and the energy consumption unit per ton of purified methanol was 6,929 MMkcal.

TABLE 12

| Gas reforming apparatus | Flow division (1) (flow path 3) (kg-mol/h) | Flow division (2) (flow path 8) (kg-mol/h) | Composition (mol %) |
| --- | --- | --- | --- |
| $CH_4$ | 3,242.7 | 2,162.2 | 78.37 |
| $C_2H_6$ | 267.6 | 178.4 | 6.47 |
| $C_3H_8$ | 104.1 | 69.4 | 2.51 |
| $C_4H_{10}$ | 47.6 | 31.7 | 1.15 |
| $C_5H_{12}$ | 16.2 | 10.8 | 0.39 |
| $C_6H_{14}$ | 5.6 | 3.8 | 0.14 |
| CO | 24.1 | 16.1 | 0.58 |
| $CO_2$ | 68.3 | 45.5 | 1.65 |
| $H_2$ | 331.3 | 220.9 | 8.00 |
| $N_2$ | 29.6 | 19.7 | 0.72 |
| $H_2O$ | 0.1 | 0.0 | 0.00 |
| $CH_3OH$ | 1.0 | 0.6 | 0.02 |
| Total | 4,138.2 | 2,759.1 | 100.00 |

TABLE 13

Steam as raw material (flow path 5) 12,776.6 kg-mol/h
Oxygen gas (flow path 9)

| $O_2$ | 3,003.2 kg-mol/h | 99.50 mol % |
| --- | --- | --- |
| $N_2$ | 15.1 | 0.50 |
| Total | 3,018.3 | 100.00 |

TABLE 14

|  | Secondary reforming outlet gas (flow path 10) | | Synthesis gas (flow path 11) | |
| --- | --- | --- | --- | --- |
|  | kg-mol/h | mol % | kg-mol/h | mol % |
| $CH_4$ | 553.6 | 1.53 | 553.2 | 2.38 |
| $CO_2$ | 2,133.5 | 5.88 | 2,121.5 | 9.13 |
| CO | 4,797.2 | 13.22 | 4,794.0 | 20.62 |
| $H_2$ | 15,697.2 | 43.26 | 15,685.7 | 67.48 |
| $N_2$ | 64.4 | 0.18 | 64.4 | 0.28 |
| $H_2O$ | 13,038.4 | 35.93 | 26.4 | 0.11 |
| Total | 36,284.3 | 100.00 | 23,245.2 | 100.00 |

TABLE 15

|  | Synthesis reactor inlet gas (flow path 12) | | Outlet gas (flow path 13) | |
| --- | --- | --- | --- | --- |
|  | kg-mol/h | mol % | kg-mol/h | mol % |
| $CH_4$ | 24,449.0 | 23.37 | 24,449.0 | 26.70 |
| $CO_2$ | 8,949.3 | 8.56 | 7,154.4 | 7.81 |
| CO | 7,997.9 | 7.65 | 3,275.4 | 3.58 |
| $H_2$ | 59,700.5 | 57.07 | 44,870.7 | 48.99 |
| $N_2$ | 3,341.7 | 3.19 | 3,341.7 | 3.65 |
| $H_2O$ | 33.9 | 0.03 | 1,835.3 | 2.00 |

TABLE 15-continued

|  | Synthesis reactor inlet gas (flow path 12) | | Outlet gas (flow path 13) | |
| --- | --- | --- | --- | --- |
|  | kg-mol/h | mol % | kg-mol/h | mol % |
| $CH_3OH$ | 130.2 | 0.13 | 6,654.1 | 7.27 |
| Total | 104,602.5 | 100.00 | 91,580.6 | 100.00 |

TABLE 16

|  | Circulating gas (flow path 14) | | Crude methanol (flow path 25) | |
| --- | --- | --- | --- | --- |
|  | kg-mol/h | mol % | kg-mol/h | mol % |
| $CH_4$ | 23,896.1 | 29.37 | 1.1 | 0.01 |
| $CO_2$ | 6,827.9 | 8.39 | 41.7 | 0.47 |
| CO | 3,203.8 | 3.94 | 0.1 | 0.00 |
| $H_2$ | 44,015.4 | 54.10 | 0.0 | 0.00 |
| $N_2$ | 3,276.9 | 4.03 | 0.0 | 0.00 |
| $H_2O$ | 7.5 | 0.01 | 2,237.8 | 25.46 |
| $CH_3OH$ | 130.2 | 0.16 | 6.507.7 | 74.06 |
| Total | 81,357.8 | 100.00 | 8,788.4 | 100.00 |

Amount of purge gas
(flow path 15) 1,521.28 kg-mol/h
(flow path 16) 500.74 kg-mol/h

Example 6

According to the flow shown in FIG. 4, hydrogen separated from a purge gas from a methanol synthesis apparatus with a PSA (pressure swing method adsorption) apparatus was introduced into the methanol synthesis apparatus to produce methanol.

In FIG. 4, hydrogen was separated from a purge gas from the flow path 17 with the PSA apparatus 27, and introduced into the methanol synthesis apparatus through the flow path 28 together with reformed gas.

The main reaction conditions in the gas reforming apparatus and the methanol synthesis apparatus were as follows.

Primary reforming inlet temperature 500° C.
Primary reforming inlet pressure 83.0 kg/cm²G
Primary reforming outlet temperature 790° C.
Secondary reforming outlet temperature 1,031° C.
Reforming reactor outlet temperature 569° C.
Reforming reactor outlet pressure 79.7 kg/cm²G
Methanol synthesis reactor inlet temperature 198° C.
Methanol synthesis reactor outlet temperature 263° C.
Methanol synthesis reactor pressure 80.0 kg/cm²G
Stoichiometric ratio in methanol synthesis reactor inlet 1.45
$CO_2$ ratio 0.995
Yield based on $CO+CO_2$ 93.9%

Tables 17 to 21 show flow amounts and compositions in main portions in the case of the production of 5,000 ton/day of methanol. As a result, there was obtained a methanol process achieving an energy consumption unit of 6.846 MMkcal per ton of purified methanol.

TABLE 17

| Gas reforming apparatus | Flow division (1) (flow path 3) (kg-mol/h) | Flow division (2) (flow path 8) (kg-mol/h) | Composition (mol %) |
| --- | --- | --- | --- |
| $CH_4$ | 3,380.6 | 2,253.5 | 78.67 |
| $C_2H_6$ | 277.4 | 184.9 | 6.45 |
| $C_3H_8$ | 107.8 | 71.9 | 2.51 |
| $C_4H_{10}$ | 49.3 | 32.9 | 1.15 |
| $C_5H_{12}$ | 16.8 | 11.2 | 0.39 |
| $C_6H_{14}$ | 5.9 | 3.9 | 0.14 |
| CO | 26.9 | 18.0 | 0.63 |
| $CO_2$ | 66.6 | 44.5 | 1.55 |
| $H_2$ | 343.6 | 229.0 | 8.00 |
| $N_2$ | 18.4 | 12.2 | 0.43 |
| $H_2O$ | 0.1 | 0.1 | 0.00 |
| $CH_3OH$ | 3.6 | 2.4 | 0.08 |
| Total | 4,297.0 | 2,864.5 | 100.00 |

TABLE 18

Steam as raw material (flow path 5) 10,809.6 kg-mol/h
Oxygen gas (flow path 9)

| $O_2$ | 3,068.4 kg-mol/h | 99.50 mol % |
| --- | --- | --- |
| $N_2$ | 15.4 | 0.50 |
| Total | 3,083.8 | 100.00 |

TABLE 19

|  | Secondary reforming outlet gas (flow path 10) | | Synthesis gas (flow path 11) | |
| --- | --- | --- | --- | --- |
|  | kg-mol/h | mol % | kg-mol/h | mol % |
| $CH_4$ | 767.3 | 2.22 | 767.3 | 3.21 |
| $CO_2$ | 1,943.7 | 5.61 | 1,943.7 | 8.13 |
| CO | 5,070.2 | 14.65 | 5,070.2 | 21.20 |
| $H_2$ | 15,613.2 | 45.11 | 16,071.3 | 67.18 |
| $N_2$ | 46.0 | 0.13 | 46.0 | 0.19 |
| $H_2O$ | 11,172.3 | 32.28 | 21.8 | 0.09 |
| Total | 34,612.7 | 100.00 | 23,920.3 | 100.00 |

TABLE 20

|  | Synthesis reactor inlet gas (flow path 12) | | Outlet gas (flow path 13) | |
| --- | --- | --- | --- | --- |
|  | kg-mol/h | mol % | kg-mol/h | mol % |
| $CH_4$ | 29,325.1 | 25.93 | 29,325.1 | 29.37 |
| $CO_2$ | 8,760.3 | 7.74 | 7,115.3 | 7.12 |
| CO | 8,806.3 | 7.79 | 3,831.0 | 3.84 |
| $H_2$ | 63,774.6 | 56.39 | 48,889.1 | 48.96 |
| $N_2$ | 1,888.0 | 1.67 | 1,888.0 | 1.89 |
| $H_2O$ | 41.7 | 0.04 | 1,699.9 | 1.70 |
| $CH_3OH$ | 497.5 | 0.44 | 7,103.9 | 7.12 |
| Total | 113,093.5 | 100.00 | 99,852.5 | 100.00 |

TABLE 21

|  | Circulating gas (flow path 14) | | Crude methanol (flow path 25) | |
| --- | --- | --- | --- | --- |
|  | kg-mol/h | mol % | kg-mol/h | mol % |
| $CH_4$ | 28,557.8 | 32.03 | 5.6 | 0.06 |
| $CO_2$ | 6,816.6 | 7.64 | 47.4 | 0.54 |
| CO | 3,736.1 | 4.19 | 0.2 | 0.00 |
| $H_2$ | 47,703.3 | 53.49 | 0.9 | 0.01 |
| $N_2$ | 1,842.0 | 2.07 | 0.0 | 0.00 |
| $H_2O$ | 19.9 | 0.02 | 2,095.7 | 23.97 |
| $CH_3OH$ | 497.0 | 0.56 | 6.595.1 | 75.42 |
| Total | 89,172.7 | 100.00 | 8,744.9 | 100.00 |

Amount of purge gas
(flow path 15) 2,140.8 kg-mol/h
(flow path 16) 1,070.4 kg-mol/h The fluidized bed catalyst reactor has the following advantages. (1) Not only gas but also catalyst particles come into contact with heat-transfer tubes in the reactor so that a high efficiency of heat transfer can be achieved. (2) The heat is well diffused in the catalyst layer so that the reaction temperature is uniform, and there is no local rise in temperature. As a result, the reactivity can be improved, and the concentration of active components ($CO+CO_2$) can be increased. The amount of a circulating gas can be therefore decreased. (3) Due to a uniform temperature distribution and high efficiency of heat transfer, the high-pressure steam recovered has an elevated pressure. (4) The pressure loss in the reactor is remarkably small as compared with a multi-tube reactor having a fixed catalyst bed. (5) The reaction temperature is uniform and there is no local rise in temperature so that the amount of byproducts is small, and the heat efficiency in the distillation and purification steps can be improved.

The process of the present invention uses a combination of a gas reforming step in which a primary reformed gas is partially oxidized and secondary reformed and the resultant high-temperature secondary reformed gas is used as a heat source for the primary reforming, and a fluidized bed catalyst reactor having the above-described advantages, and the present invention defines the composition of a feed gas to the reactor. When the reaction conditions and process are selected such that they are suited for the defined composition of a feed gas, there can be provided a process for the production of methanol, which process permits an increase in the capacity of an apparatus for the production of methanol with high energy efficiency.

What is claimed is:

1. A process for the production of methanol, comprising a primary reforming step of catalytically reacting a hydrocarbon as a raw material with steam, a partial oxidation step of gas fed from said primary reforming step by adding an oxygen gas, a secondary reforming step of catalytically reacting a gas fed from said partial oxidation step with steam, a step of using a high-temperature gas obtained from the secondary reforming reaction step as a heat source for the primary reforming step, a synthesis gas preparation step of condensing the gas used as said heat source and separating steam from the gas used as said heat source to prepare a synthesis gas, and a methanol synthesis step of introducing the synthesis gas into a methanol synthesis reactor, wherein, the hydrocarbon as a raw material is at least one member selected from the group consisting of natural gas, liquified propane gas and naphtha; and part of a gas from the methanol synthesis reactor is fed as circulating gas to the methanol synthesis reactor together with the synthesis gas, a remaining part of the gas from the methanol synthesis reactor is fed as purge gas to said primary reforming step together with the hydrocarbon as a raw material, and at least one step selected from the following steps (a), (b), (c) and (d) is carried out to bring the molar ratio of hydrogen to carbon oxides in a feed gas to be introduced into the methanol synthesis reactor, represented by $\{H_2/(2CO+3CO_2)\}$, into a range of from 1.0 to 2.7 and to bring the molar ratio of $CO_2/CO$ in the feed gas into a range of from 0.6 to 1.2:

(a) a step of feeding the synthesis gas from which carbon dioxide gas is removed to the methanol synthesis reactor together with the circulating gas;

(b) a step of removing carbon dioxide gas from part of the purge gas, and feeding the purge gas from which the carbon dioxide is removed into the methanol synthesis reactor together with the synthesis gas and the circulating gas;

(c) a step of cooling the gas from the methanol synthesis reactor to separate it into a crude methanol in which carbon dioxide gas is dissolved and a gas, and feeding the gas to the methanol synthesis reactor as the circulating gas together with the synthesis gas; and (d) a step of recovering hydrogen from part of the purge gas, and feeding the hydrogen to the methanol synthesis reactor together with the synthesis gas and the circulating gas.

2. A process according to claim 1, wherein the process comprises a. a primary reforming step of mixing part of the purge gas with the hydrocarbon as a raw material to prepare a mixed gas, adjusting 40 to 80 mol % of the mixed gas to have a molar ratio (S/C) of steam (S) to hydrocarbon (C) of 1.5 to 4.0 and introducing the adjusted mixed gas into the primary reforming step to carry out the primary reforming reaction such that outlets of reaction tubes show a pressure of 25 to 95 atmospheric pressure and a temperature of 700° to 800° C., b. a partial oxidation step of adding oxygen gas in an amount of 0.40 to 0.46 mol per mole of total carbon of hydrocarbon as a raw material to a primary reformed gas and a remainder of the above mixed gas to carry out a partial oxidation, and c. a step of using a secondary reformed gas obtained from the secondary reforming step as a heat source for the primary reforming step, separating unreacted steam by heat recovery and cooling, and introducing the synthesis gas into the methanol synthesis reactor.

3. A process according to claim 1, wherein the synthesis gas is introduced into the methanol synthesis reactor through a compression step.

4. A process according to claim 1, wherein carbon dioxide gas is removed by allowing crude methanol obtained from the methanol synthesis step to absorb the carbon dioxide gas.

5. A process according to claim 4, wherein the crude methanol is cooled with at least one of the heat evaporation of liquid oxygen to be used in the gas reforming step and the sensible heat of low-temperature oxygen to be used in the gas reforming step before absorbing carbon dioxide gas.

6. A process according to claim 1, wherein hydrogen is separated with a pressure swing adsorption apparatus.

7. A process according to claim 1, wherein the purge gas from which hydrogen has been separated is used as a fuel for a gas turbine engine.

8. A process according to claim 1, wherein the purge gas is partly used as a fuel for a gas turbine engine.

9. A process according to claim 1, wherein methanol synthesis reactor is a fluidized bed catalyst reactor.

* * * * *